(12) United States Patent
Rytz et al.

(10) Patent No.: US 12,076,526 B2
(45) Date of Patent: Sep. 3, 2024

(54) PATCH DELIVERY DEVICE WITH SKIN CONTACT SENSOR

(71) Applicant: Ypsomed AG, Burgdorf (CH)

(72) Inventors: Bernhard Rytz, Zollbrück (CH); Simon Scheurer, Bern (CH); Krista Kappeler, Bern (CH)

(73) Assignee: Ypsomed AG, Burgdorf (CH)

( * ) Notice: Subject to any disclaimer, the term of this patent is extended or adjusted under 35 U.S.C. 154(b) by 873 days.

(21) Appl. No.: 17/017,468

(22) Filed: Sep. 10, 2020

(65) Prior Publication Data

US 2020/0405952 A1    Dec. 31, 2020

Related U.S. Application Data

(63) Continuation of application No. PCT/IB2019/052421, filed on Mar. 26, 2019.

(30) Foreign Application Priority Data

Mar. 27, 2018  (EP) .................................... 18164145

(51) Int. Cl.
*A61M 5/142*           (2006.01)
(52) U.S. Cl.
CPC ..... *A61M 5/14248* (2013.01); *A61M 2205/13* (2013.01)
(58) Field of Classification Search
CPC ...................... A61M 2205/13; A61M 5/14248
(Continued)

(56) References Cited

U.S. PATENT DOCUMENTS 3,260,147 A    7/1966  Farabee
3,260,149 A    7/1966  Deaver
(Continued)

FOREIGN PATENT DOCUMENTS

EP    2512552 B1    2/2015
EP    3260147 A1    12/2017
(Continued)

OTHER PUBLICATIONS

Extended European Search Report received for European patent application No. 18164145.7, issued on Nov. 12, 2018, 6 page.
(Continued)

*Primary Examiner* — Theodore J Stigell
*Assistant Examiner* — Nidah Hussain
(74) *Attorney, Agent, or Firm* — Dorsey & Whitney LLP (57) ABSTRACT

A patch delivery device includes a bottom housing part, a delivery element for subcutaneous delivery of a liquid to a patient, an adhesive patch for attaching the bottom housing part to the skin of the patient, a capacitive sensor with an electrode configuration including a plurality of skin contact sensitive electrodes, and a release liner covering a patient-side adhesive layer of the adhesive patch prior to adhering to the patient's skin. The release liner includes an electrically conductive area extending over at least a portion of the electrode configuration of the capacitive sensor before being removed from the adhesive patch. Providing the release liner with a conductive area gives rise to a discernible change in capacitive response of the sensor electrodes upon release liner removal that enables sensing a removal of a release liner covering a patient-side adhesive layer prior to attachment to the skin of a patient.

18 Claims, 3 Drawing Sheets

(58) Field of Classification Search
USPC .......................................................... 604/180
See application file for complete search history.

(56) References Cited

U.S. PATENT DOCUMENTS

| | | | |
|---|---|---|---|
| 3,260,151 | A | 7/1966 | Jones |
| 3,909,910 | A | 10/1975 | Rowe et al. |
| 4,019,512 | A | 4/1977 | Tenczar |
| 5,019,047 | A | 5/1991 | Kriesel |
| 6,382,442 | B1 | 5/2002 | Thibault et al. |
| 6,679,529 | B2 | 1/2004 | Johnson et al. |
| 6,843,782 | B2 | 1/2005 | Gross et al. |
| 8,315,687 | B2 | 11/2012 | Cross et al. |
| 9,248,232 | B2 | 2/2016 | Yodfat et al. |
| 9,427,529 | B2 | 8/2016 | Cabiri |
| 10,758,721 | B2 | 9/2020 | Sonderegger et al. |
| 2001/0056262 | A1 | 12/2001 | Cabiri et al. |
| 2003/0030272 | A1 | 2/2003 | Johnson et al. |
| 2004/0116866 | A1 | 6/2004 | Gorman et al. |
| 2008/0048436 | A1 | 2/2008 | Matkovich et al. |
| 2009/0095290 | A1 | 4/2009 | Cain et al. |
| 2011/0166512 | A1* | 7/2011 | Both ................ A61M 5/14248 604/152 |
| 2012/0316506 | A1 | 12/2012 | Sonderegger et al. |
| 2014/0008366 | A1 | 1/2014 | Genosar |
| 2015/0105691 | A1 | 4/2015 | Hadvary et al. |
| 2015/0217058 | A1 | 8/2015 | Hooven et al. |
| 2015/0320990 | A1 | 11/2015 | Burton et al. |
| 2016/0089056 | A1* | 3/2016 | Limaye ................ A61M 5/46 600/409 |
| 2016/0199568 | A1 | 7/2016 | Mcnall et al. |
| 2016/0220798 | A1 | 8/2016 | Netzel et al. |
| 2016/0256665 | A1 | 9/2016 | Doshi et al. |
| 2016/0310663 | A1 | 10/2016 | Dantsker |
| 2016/0310665 | A1 | 10/2016 | Hwang et al. |
| 2017/0020423 | A1 | 1/2017 | Fujita et al. |
| 2017/0259015 | A1 | 9/2017 | Caspers |
| 2018/0353704 | A1 | 12/2018 | Helmer |
| 2019/0240417 | A1 | 8/2019 | Hostettler et al. |
| 2019/0274924 | A1 | 9/2019 | Barmaimon et al. |
| 2019/0374707 | A1 | 12/2019 | Damestani et al. |
| 2020/0001068 | A1 | 1/2020 | Donze et al. |
| 2020/0297917 | A1 | 9/2020 | Helmer et al. |
| 2020/0316290 | A1 | 10/2020 | Bourelle et al. |
| 2020/0397984 | A1 | 12/2020 | Reed et al. |
| 2020/0405950 | A1 | 12/2020 | Burren et al. |
| 2020/0405951 | A1 | 12/2020 | Burren et al. |
| 2020/0405952 | A1 | 12/2020 | Rytz et al. |
| 2021/0001048 | A1 | 1/2021 | Schrul et al. |
| 2021/0030949 | A1 | 2/2021 | Damiano et al. |
| 2021/0038805 | A1 | 2/2021 | Goldstein |
| 2021/0093849 | A1 | 4/2021 | Stumpe et al. |
| 2021/0128844 | A1 | 5/2021 | Boyaval et al. |
| 2021/0170095 | A1 | 6/2021 | Diperna et al. |
| 2021/0260279 | A1 | 8/2021 | Boyaval et al. |

FOREIGN PATENT DOCUMENTS

| | | |
|---|---|---|
| EP | 3260149 A1 | 12/2017 |
| EP | 3260151 A1 | 12/2017 |
| EP | 3052166 B1 | 4/2019 |
| EP | 3539591 A1 | 9/2019 |
| EP | 3539592 A1 | 9/2019 |
| EP | 3539596 A1 | 9/2019 |
| EP | 3545997 A1 | 10/2019 |
| EP | 3582825 A1 | 12/2019 |
| EP | 3697475 A1 | 8/2020 |
| WO | 9959665 A1 | 11/1999 |
| WO | 2006067217 A2 | 6/2006 |
| WO | 2008068695 A1 | 6/2008 |
| WO | 2011015659 A1 | 2/2011 |
| WO | 2011064780 A2 | 6/2011 |
| WO | 2011075099 A1 | 6/2011 |
| WO | 2017089271 A1 | 6/2017 |
| WO | 2017089286 A1 | 6/2017 |
| WO | 2017219155 A1 | 12/2017 |
| WO | 2018151890 A1 | 8/2018 |
| WO | 2019175688 A1 | 9/2019 |
| WO | 2019175689 A1 | 9/2019 |
| WO | 2019175690 A1 | 9/2019 |
| WO | 2019186375 A1 | 10/2019 |

OTHER PUBLICATIONS

International Search Report and Written Opinion received for International Application No. PCT/IB2019/051357 mailed on May 7, 2019, 12 pages.

International Search Report and Written Opinion received for International Application No. PCT/IB2019/051358, mailed on May 15, 2019, 9 pages.

International Search Report and Written Opinion received for International Application No. PCT/IB2019/051359, mailed on May 15, 2019, 10 pages.

International Search Report and Written Opinion received for International Application No. PCT/IB2019/052421, mailed on Aug. 6, 2019, 10 pages.

International Preliminary Report on Patentability received for International Application No. PCT/IB2019/051357, mailed on Sep. 15, 2020.

International Preliminary Report on Patentability received for International Application No. PCT/IB2019/051358, mailed on Sep. 15, 2020.

International Preliminary Report on Patentability received for International Application No. PCT/IB2019/051359, mailed on Sep. 15, 2020.

International Preliminary Report on Patentability Received for International Application No. PCT/IB2019/052421, mailed on Sep. 29, 2020, 6 pages.

* cited by examiner

PATCH DELIVERY DEVICE WITH SKIN CONTACT SENSOR

CROSS-REFERENCE TO RELATED APPLICATIONS

This application claims priority to International Patent Application No. PCT/IB2019/052421, filed Mar. 26, 2019, entitled "PATCH DELIVERY DEVICE WITH SKIN CONTACT SENSOR," which in turn claims priority to European Patent Application No. 18164145.7, filed Mar. 27, 2018, entitled "PATCH DELIVERY DEVICE WITH SKIN CONTACT SENSOR", each of which is incorporated by reference herein, in the entirety and for all purposes.

TECHNICAL FIELD

Implementations relate to drug delivery systems for delivering, administering, injecting, infusing and/or dispensing liquids comprising a medicament or active ingredient, and more particularly relate to patch delivery devices configured for sensing proper adherence to the skin of a patient.

BACKGROUND

A variety of diseases require regular treatment by subcutaneous, intradermal, or intramuscular administration of a medicament. In response, a number of drug delivery devices have been developed to support a patient's health in conveniently and controllably delivering a precise amount of drug in a self-administration process. Delivery devices include injection devices that are removed from the injection site after each medication event or drug delivery process, and infusion devices or pumping devices with a fluid channel into the body of the patient that remains in use for a prolonged period of time.

Disposable single-use injection devices include auto-injectors and patch injection devices for delivering a fixed or variable dose of drug from a container through a cannula or injection needle. Neither the latter nor the medicament container are intended to be manipulated, let alone replaced, by the user of an auto-injector or patch injection device. Patch injection devices or ready-to-use pre-filled wearable bolus injectors (WBI) or on-body delivery systems (OBDS) are mounted, attached, patched or adhered to the skin of the patient in view of an imminent extended single dose injection taking at least thirty seconds to complete. Patch injection devices were developed for the treatment of diseases like cardiovascular diseases, auto immune diseases or cancer, and are suitable for the delivery of medicaments which comprise injectable liquids with a high viscosity, and/or which are to be administered in larger single dose volumes of up to five or even ten milliliters.

Infusion devices include pump devices for continual delivery of a regular or basal amount of medication through a cannula that remains in the injection site for an extended period of time of up to three days. Disposable single-use or semi-disposable infusion devices include patch infusion pumps or wearable basal infusion devices that are mounted, attached, patched or adhered to the skin of the patient in view of an uninterrupted infusion and for delivery of multiple adjustable doses superimposed on a basal rate. The disposable part includes at least a skin-contact area and a cannula that are not intended to be replaced but disposed of after having been in use for a period between thirty minutes and several days. Patch pumps have remote controls and are directly worn on the body, thus eliminating the need for long catheters and direct pump access, and are preliminarily being used for the treatment of diabetes.

WO 2006/067217 A2 relates to a skin mountable medical device comprising sensing sensor means adapted to detect a property of the device that can be indicative of a problematic condition relating to the interface of the device with the subject. The device further comprises circuitry for processing signals from the sensor means and for indicating that a predetermined condition associated with the interface of the device with the subject has been detected. The sensor means include first and second capacitor plates arranged laterally adjacent on a mounting surface, a capacitive circuit being established when the mounting surface is arranged on a skin surface.

US 2017/259015 discloses a single-use, skin-patch type of large-volume or bolus injection device comprising an adhesive surface for attachment to the skin and a plurality of capacitive, resistive, or temperature contact sensors located at discrete locations on a contact surface of the device. The plurality of contact sensors is configured to output a signal representing a degree of detachment of the device from the injection site as may result from an otherwise unnoticed degradation in the adhesive layer that attaches the device to the injection site. An alarm and control function outputs an alert to the user based on the signal received from the sensors and slows or even interrupts the injection in case the degree of detachment jeopardizes further save injection. The contact sensors are arranged around an aperture at a bottom portion of the device through which a delivery cannula protrudes into the tissue of the patient during use of the device for delivery of the medicament.

EP 3260151 A1 discloses a patch device with a bottom housing part, a capacitive sensor, an adhesive patch with a first adhesive layer contacting the bottom housing part and a second adhesive layer to contact a target, and a release liner made of coated paper or a thin sheet of plastic that covers the second adhesive layer prior to use of the device. The conductive elements of the sensor are embedded in the adhesive patch, or integrated into the bottom housing part, or otherwise attached to the patch or part. The release liner or peel-off foil prevents unintended adhesion and contamination of the second adhesive layer. Removal of the release liner may be combined with other functionalities such as switching or activating electrical circuitry or removing a sterile barrier of a fluid path or of a passage for the cannula.

WO 2008/068695 A1 discloses a release liner for an electrocardiogram (ECG) monitoring device that can be used for patient survey prior to the removal of any release liner portion. The release liner has electrode areas aligned with and covering electrodes of the ECG monitoring device. The electrode areas are formed of a conductive material such as metallic foil and extend from one side to the other of the release liner, with a same lateral extension as the covered electrodes. The electrode areas provide conduction paths by which the ECG signal can be detected by the ECG monitoring device prior to any release liner removal.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

SUMMARY

It is an objective to improve safe use of a patch delivery device and to identify a removal of a release liner covering a patient-side mounting or adhesive layer prior to attachment of the latter to the skin of a patient. This objective is achieved by a patch delivery device and a sensor patch according to the present disclosure.

According to implementations, a patch delivery device such as a patch pump or patch injector includes a bottom housing part or base plate, a delivery element or cannula for subcutaneous delivery of a liquid to a patient, an adhesive patch for attaching the bottom housing part to the skin of the patient, a capacitive sensor with an electrode configuration including a plurality of electrodes sensitive to skin contact as disjoint areas independently connected or interfaced to a capacitance measuring unit of the device, and a release liner covering and protecting a patient-side adhesive layer of the adhesive patch prior to adhering to the skin of the patient. The release liner includes an electrically conductive area extending over, or covering, at least a part of the electrode configuration of the capacitive sensor before being removed from the adhesive patch. The conductive area may be provided on and/or embedded in a non-conducting layer of the release liner, in particular printed, coated, glued or otherwise applied onto a surface of the non-conducting layer.

The plurality of electrodes may be arranged laterally offset from each other in an electrode layer parallel to a skin contact surface of the bottom housing part. The non-conducting layer is made of a nonconductive material such as a piece of Kraft paper, a thin sheet of plastic, or a polymeric film, and supports the conductive area in its entirety, such that the latter does not provide a conductive path between the two surfaces of the release liner. Providing the release liner with a conductive area electrically isolated from the sensor electrodes when covering the patient-side adhesive layer in the intended or original orientation gives rise to a discernible change in a capacitive response of the sensor electrodes upon release liner removal, and thus enables the device to automatically detect removal of the release liner. As an additional benefit, a larger relative change in capacitance is observable when attaching the device without release liner to the injection site as compared to a preceding test approach of the injection site with the release liner still in place. In addition, or complementary, to use of the capacitive electrodes for determining a degradation in the adhesion to the human skin, a patch delivery device according to the invention detects electrode signals prior to device adherence. Test or dummy skin contacts may thus be identified, and inadvertent triggering or other handling errors may be prevented.

In some implementations, the capacitive sensor includes an aperture electrode and an auxiliary electrode, the electrodes being arranged adjacent to, or facing, separate portions or halves or distinct portions or halves of a skin contact area of the bottom housing part, and may be placed at a distance of at least half a largest linear dimension or extent, e.g., length, of the bottom housing part from each other. The conductive release liner area extends at least in part over both corresponding electrode areas. In addition to confirmation of complete adherence and/or absence of partial detachment, such electrode configuration allows detecting removing or peeling-off of the release liner in a direction between the two electrodes through time-resolved capacitance tracking.

In some implementations, the capacitive sensor includes a first aperture electrode and a second aperture electrode arranged on opposite sides of an aperture of the adhesive patch corresponding to a location of the delivery element, where a conductive area of the release liner extends over an electrode area of both aperture electrodes. The conductive area may extend over substantially the entire surface area of the non-conducting layer of the release liner and/or the skin contact surface of the bottom housing part.

In some implementations, the capacitive sensor includes a first aperture electrode and a second aperture electrode, where the conductive area of the release liner covers the two corresponding electrode areas to a different extent or degree or fraction when the release liner is mounted in the intended or original configuration with respect to the sensor electrodes. In a most asymmetric coverage, the first aperture electrode area maybe entirely covered, or hidden, by the conducting area while the second aperture electrode area is not covered, or shielded, at all. Such configurations of distinctive coverage results in distinct capacitive responses from the two electrodes upon release liner removal, which enables identification of the release liner removal activity in real time prior to attachment of the device. The difference in response signal is most prominent in this most asymmetric case, whereas covering one half of both electrode areas is unlikely to result in distinguishable capacitance changes. Response signals with different characteristics may also be provided when testing or using a dummy for patient skin prior to release liner removal.

In a further embodiment, the patch drug delivery device is a patch injection device or a wearable bolus injector for delivering a single dose or bolus volume from a container through a single use cannula in an injection process taking at least thirty seconds and preferably between five and thirty minutes. Patch injection devices were developed for injectable liquids with a high viscosity of at least 1 cP (0.050 kgnrV1), such as at least 15 cP, or even at least 50 cP. Alternatively, the patch drug delivery device may be a basal type patch infusion pump device. Implementations may also be applicable to an infusion set supporting a cannula that in turn is connected to a non-patch pump device via a flexible catheter tubing or fluid conduit, where an adhesion of the infusion set to the patient skin requires monitoring, and for which release liner removal is confirmed prior to needle insertion.

In another embodiment, at least the sensor electrodes of the capacitive sensor are part of or embedded in the adhesive patch, and may be reconfigured or shifted without adapting the housing of the device. Alternatively, the sensor electrodes are integrated into the bottom housing part of the device, which may facilitate connection of the electrodes to the capacitance measuring unit.

According to some implementations, a sensor patch for a patch delivery device with a bottom housing part and a delivery element for subcutaneous delivery of a liquid to a patient is provided. The sensor patch comprises an adhesive patch for adhering to the bottom housing part, a capacitive sensor with a plurality of electrodes integrated in or printed onto the adhesive patch, and adapted to be connected to a capacitance measuring unit of the delivery device. The sensor patch further comprises a release liner including a conductive area covering a patient-side or skin-contact layer of the adhesive patch.

In some implementations of the sensor patch, the patient-side layer of the adhesive patch is a skin-adhesive layer for adhering the sensor patch to the skin of the patient. Alternatively, skin contact may be established by mounting or attaching the device with the sensor patch to the skin of the patient, and by securing the device in this position by tightly wrapping a non-adhesive bandage, belt or strap around the patient and the device.

BRIEF DESCRIPTION OF THE DRAWINGS

The reference symbols used in the drawings, and their primary meanings, are listed in summary form in the list of designations. In principle, identical parts are provided with the same reference symbols in the figures.

DETAILED DESCRIPTION

Figure 1A:
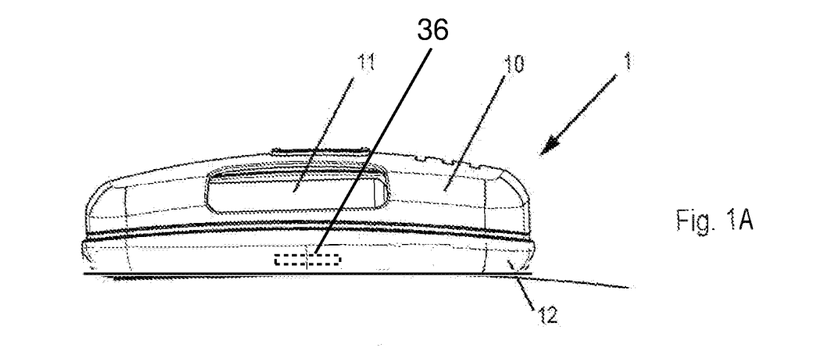
FIGS. 1A and 1B illustrate a side view and a top view, respectively, of a patch delivery device according to implementations of the present disclosure.
Figure 1B:
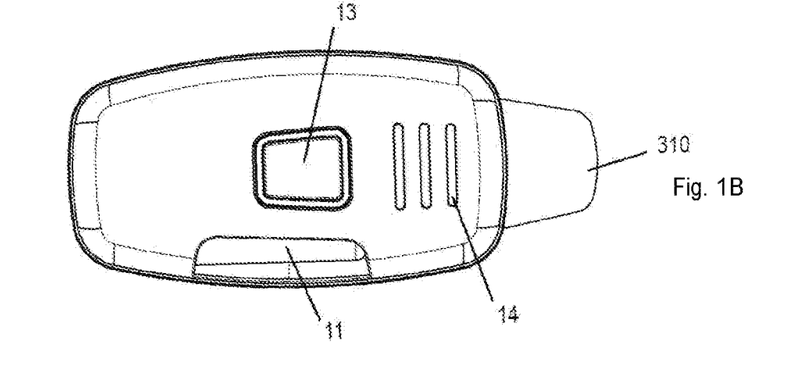

FIGS. 1A and 1B depict a side view and a top view, respectively, of a patch delivery device comprising a housing 1 with a cover housing part 10 including a window 11 for viewing a cartridge, a bottom housing part or base plate 12, a release button 13 for activating the device and/or starting the injection, and an optical indicator 14 such as an LED. A patient facing side or skin contact area of the bottom housing part is to be adhered or attached to the skin of a patient by means of an adhesive patch, of which a release liner tab 310 laterally extends beyond the skin contact area. Exemplary sub-assemblies and components of the patch delivery device include a cartridge retainer for holding a cartridge with a liquid medicament to be expelled by a moving piston, a needle insertion mechanism for inserting a cannula into the skin of the patient, a fluid path for connecting the cannula to the cartridge, and a drive means for expelling the liquid and/or driving the needle insertion mechanism. These sub-assemblies are amply described for instance in EP 3260151 A1, the disclosure of which is hereby incorporated by way of reference in its entirety.

Figure 2:
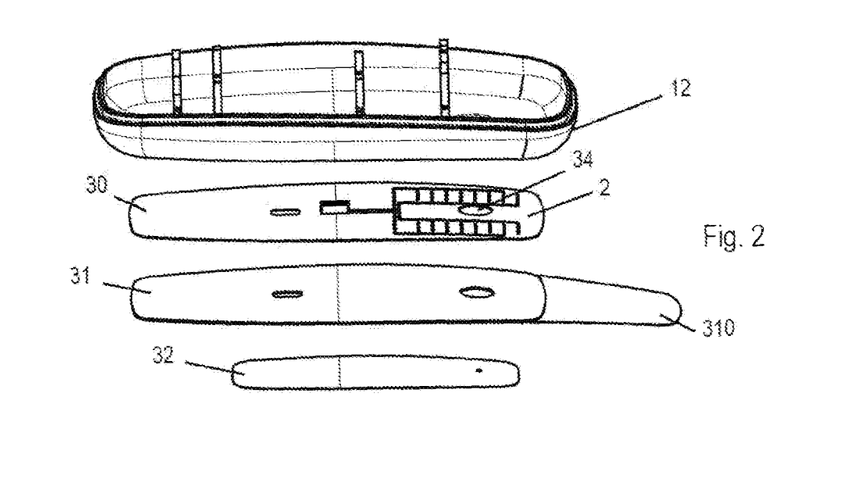
FIG. 2 illustrates an exploded view of the patch delivery device of FIGS. 1A and 1B.

FIG. 2 depicts an exploded view of the bottom housing part 12 of the housing 1, a capacitive sensor 2, an adhesive patch 30, a release liner or peel-off layer 31, and an auxiliary sticker or adhesive layer 32. The adhesive patch 30 includes an aperture or passage 34 such as a punctured hole, corresponding to a location of the cannula 35 of the delivery device, through which aperture 34 the cannula 35 will extend during delivery. The capacitive sensor 2 comprises conductive elements that are embedded in, printed onto, or otherwise attached to the adhesive patch 30 to form a sensor patch. Alternatively, the capacitive sensor 2 may be integrated in the bottom housing part 12, printed onto, or otherwise attached to the patient facing side thereof. The adhesive patch 30 generally includes a multilayer composite with, on opposite sides of a base layer, a device side adhesive layer for permanently attaching the adhesive patch to the patient side of the delivery device, and a patient side adhesive layer for non-permanently attaching the adhesive patch to the skin of the patient. The adhesive patch 30 may include additional layers, such as a shielding layer protecting the patch delivery device against electromagnetic fields or humidity. The release liner may be constructed of coated paper or a thin sheet of plastic, and prevents unintended adhesion or contamination of the patient side adhesive layer of the adhesive patch. The release liner 31 includes a tab 310 that laterally extends beyond the contour of the adhesive patch. A user may grasp the tab 310 for easy removal of the release liner 31 and corresponding exposure of the patient side adhesive layer. The bottom housing part 12 includes an opening configured as an egress or ingress port for the cannula 35 at a location corresponding to the aperture 34, and this opening may be covered by an aseptic cover or sterile barrier prior to needle insertion. The auxiliary sticker or adhesive foil 32 may be provided for connecting the release liner 31 to the aseptic cover, to ensure concurrent removal of the release liner 31 and the aseptic cover. To that end, the release liner 31 may also include a passage through which a device side adhesive part of the auxiliary sticker 32 contacts the aseptic cover.

An activation of the device even from an unpowered state may occur via the button 13 or via another mechanical switch, for instance, coupled to a cardboard box or to a soft packaging of the delivery device that the user removes to gain access to the device. Likewise, the release liner 31 and in particular the tab 310 may be connected in a tear-proof manner to a switch that may be switched to a device-activated state connecting a power source to a control unit, or to a removable insulator positioned between the power source and control unit circuitry. The delivery device may alternatively be activated or switched from a stand-by or low-power-consumption state in which the control unit monitors an activation sensor on a continuous or continual basis to an activated state. For instance, RFID sensing circuitry or an electromagnetic activation sensor may be employed to detect removal of the release liner.

The needle insertion mechanism for insertion of an insertion element, such as an injection needle or cannula 35, into the skin of the patient may additionally be equipped with a needle retraction device, to retract the insertion element into the delivery device before removal from the injection site. For instance, a needle insertion mechanism may either insert first a needle together with a soft cannula surrounding the needle, where the needle is retracted prior to delivery of the medication through the soft cannula, or may insert a hollow injection needle or rigid cannula, e.g., made of stainless steel, in the patient's tissue and may also be used for subsequent delivery. The insertion mechanism for inserting the delivery element may be a mechanical spring-based insertion mechanism. Alternatively, the insertion mechanism may include an electric motor and a gear mechanism that causes insertion of the insertion element into the user. Alternatively, the insertion mechanism may be a gas or fluid pressure operated mechanism, in which case the driving energy source is a reservoir of pressurized gas.

In any case, start of medication delivery is only enabled after, and as long as, attachment of the device to the skin has been, or is being, confirmed. Skin proximity, and therefore presumed attachment of the delivery device, is detected by the capacitive sensor measuring a difference in capacity between a non-skin adhered and skin adhered status of the delivery device. Detecting the human skin is a self-capacitance measurement similar to a capacitive sensing button solution of a touch pad. The capacitive sensor includes conductive electrodes, traces or pads arranged in a way to create parasitic capacitors between each of the electrodes and ground node. Because the human skin will have a small intrinsic capacitance and/or admittance to ground, the capacitance of the parasitic capacitors will increase when, and as long as, the corresponding electrode is in contact or in proximity to the skin.

Figure 3:
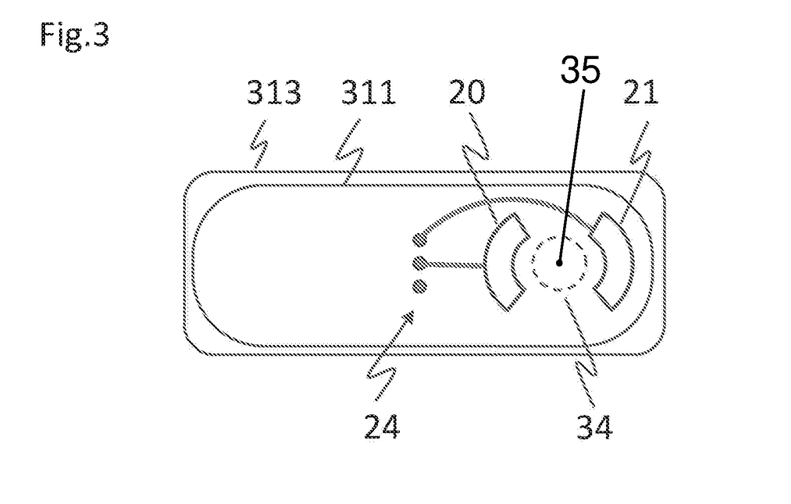
FIG. 3 illustrates an electrode arrangement and release liner according to a first embodiment.

FIG. 3 depicts a first embodiment of an electrode arrangement of a capacitive sensor with a first release liner. The capacitive sensor includes a first aperture electrode 20 and a second aperture electrode 21 arranged on opposite sides of a circular aperture or passage 34 of an adhesive patch. The aperture 34 corresponds to a location of the cannula 35 of the delivery device, through which aperture 34 the cannula 35 will extend during drug delivery. The two aperture electrodes 20, 21 are conductively connected, via corresponding traces or contacts, to a sensor interface 24 providing access to a capacitance measuring unit 36 of the delivery device. In the case of a sensor patch integrating the sensor electrode arrangement, this sensor interface 24 provides a reliable electrical contact, which may be established by means of spring-biased contact pins in the bottom housing part 12. The first release liner includes a non-conductive layer or sheet 313 and a first conductive area 311 extending over the electrode area of both aperture electrodes 20, 21 and, apart from a border area, essentially covers the entire area of the non-conductive layer 313.

In this embodiment, the signals provided by the two aperture electrodes 20, 21 are essentially identical. If the delivery device contacts the patient skin with the release liner still being in place, the signals decrease somewhat due to skin contact and corresponding increase in self capacitance. Upon removal of the release liner including the conductive area 311, a signal value increases for both aperture electrodes 20, 21 following a discernible change in capacitive response of the two electrodes. Subsequently, contacting the patient skin for a regular injection will lead to a simultaneous drop in both electrode signals 20, 21, distinctly more pronounced in magnitude than in the test approach before removal of the release liner.

Figure 4A:
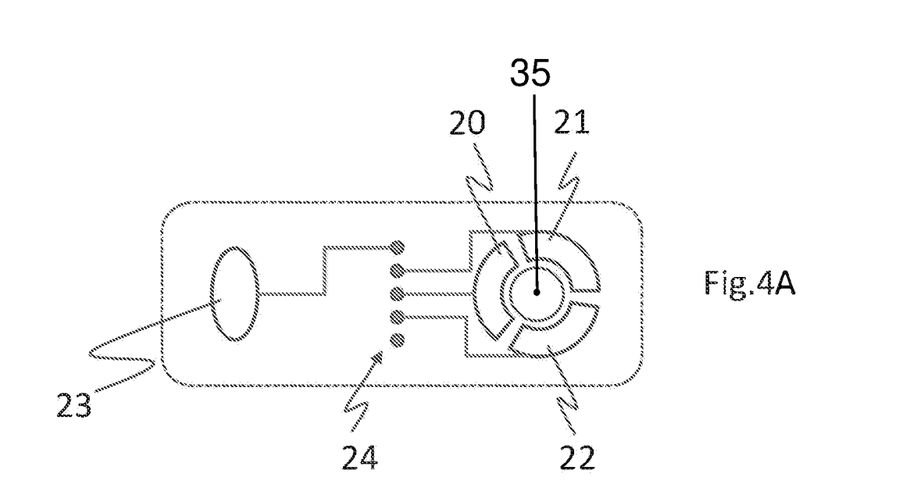
FIGS. 4A and 4B illustrate an electrode arrangement and release liner according to a second embodiment.
Figure 4B:
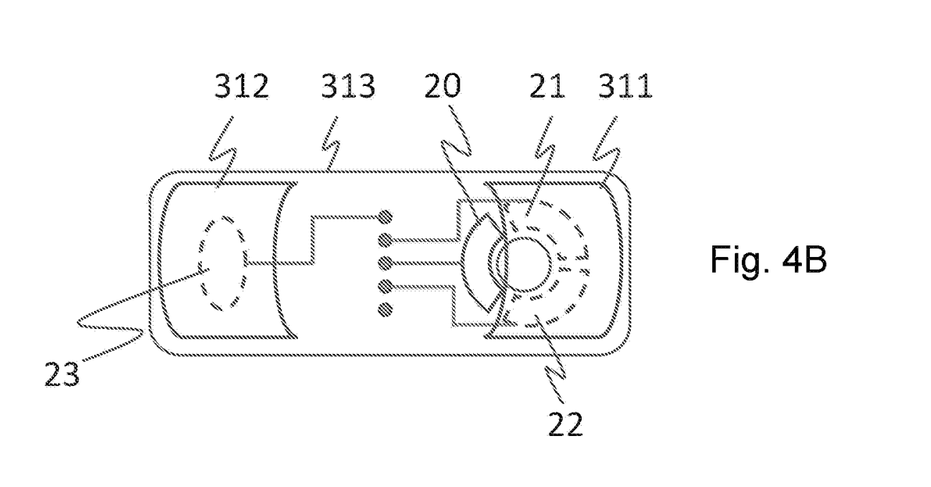

FIGS. 4A-4B depict a second embodiment of an electrode arrangement of a capacitive sensor in which FIG. 4A depicts the electrode arrangement of the capacitive sensor, and FIG. 4B depicts the electrode arrangement and a matching second release liner. The sensor includes three aperture electrodes 20, 21, 22 forming and surrounding a circular aperture or passage corresponding to a location of the cannula 35 of the delivery device, through which aperture the cannula 35 will extend during drug delivery. The aperture electrodes 20, 21, 22 are placed adjacent to a first half of the skin contact area, with an auxiliary electrode 23 being provided adjacent to a second half of the skin contact area of the bottom housing part, at a distance of at least half a largest linear dimension or extent, e.g., length, of the bottom housing part from each other. All four electrodes 20, 21, 22, 23 are conductively connected, via corresponding traces or contacts, to a sensor interface 24 providing access to a capacitance measuring unit 36 of the delivery device. In the case of a sensor patch integrating the sensor electrode arrangement, this sensor interface 24 needs to provide a reliable electrical contact, which may be established by means of spring-biased contact pins in the bottom housing part.

The second release liner is shown superimposed to the second electrode configuration. The release liner includes a non-conductive layer or sheet 313, a first conductive area 311 adjacent to and covering two of the aperture electrodes 21, 22, and a second conductive area 312 adjacent to and covering the auxiliary electrode 23. Both electrically conductive areas 311, 312 are part of a coating layer embedded in, or printed on either side of, the non-conductive layer 313 of the release liner, and influence a capacitance of the electrodes of the capacitive sensor as will be apparent below. The conductive areas 311, 312, such as conductive area 311, may take different shapes extending over at least a part of the electrode configuration, for instance, where at least one electrode is covered to a lower degree than another one.

Figure 5:
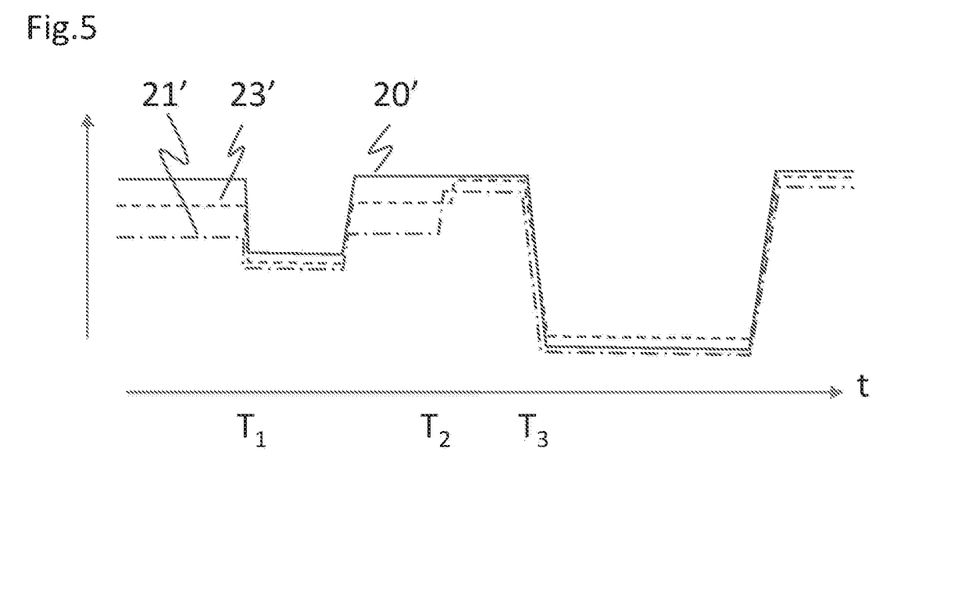
FIG. 5 is a graph showing three self-capacitance signals of the electrode arrangement of FIGS. 4A and 4B.

FIG. 5 depicts three measured signals 20', 21', 23' indicative of a self-capacitance for each of the three aforementioned electrodes 20, 21, 23 over time. The signal of electrode 22 is essentially equal to the signal 21 and for that reason has been omitted. Three events are clearly distinguishable via the characteristic electrode signals. The first event (starting at T 1) corresponds to the delivery device approaching the patient skin for a short period of time, such as necessary for the patient to test whether he/she is comfortable with a proposed injection site. Such test or dummy contact occurs with the release liner still being in place and covering the patient side adhesive layer of the adhesive patch in turn mounted to the contact side of the bottom housing part. Due to the skin contact, all signals decrease, which corresponds to an increase in capacitance, wherein the signal 20' of the uncovered electrode shows a distinctly larger drop than the other three signals. The test contact sequence may be repeated to find a suitable injection site, and is completed by removing the device from the injection site for release liner removal. The second event (starting at T2) is the release liner removal, which leads to an increase in signal value 21', 23' for the two previously covered electrodes, while the signal 20' of the uncovered electrode 20 remains essentially unchanged. Upon closer inspection the one signal 23' of the auxiliary electrode 23 is revealed to be lagging behind compared to the signal value 21', which is indicative of the corresponding part of the release liner 312 being removed after removal of the release liner 311. The electrode configuration hence allows detecting removal or peel-off of the release liner in a direction between the two electrodes through time-resolved capacitance tracking. The third event (starting at T3) finally is a regular injection, with all four signals dropping simultaneously. While the signals depicted are of capacitive nature and rely on a galvanic separation between the sensor electrodes and the conductive area of the release liner, an electrical contact provided by the conductive area, for instance as a shortcut between selected electrodes, may be exploited in addition to the capacitive signal, or even alternatively thereto at least for the purpose of release liner removal detection.

The presence of an electrically conductive area, at floating voltage, adjacent to and facing a sensor electrode primarily tends to increase a capacitance of a circuit comprising the electrode. When approaching or even contacting the skin of the patient, an expected increase in capacitance due to the capacitive properties of the skin is reduced as a consequence of a shielding effect of the conductive area. In other terms, a conductive area reduces a relative increase in capacitance when approaching the patient skin as compared to a conventional release liner without conductive area, or as compared to no release liner at all. An automated distinction between successively recorded patient skin approaches with and without the release liner is thus made possible. Such distinction may complement an independent detection of a release liner removal activity having occurred between the two patient skin approaches. Such distinction contributes to a reliable identification of an attachment of the delivery device to the patient's skin by way of the adhesive patch, as a prerequisite for subsequent needle insertion, and as opposed to a test or dummy approach, which contributes to an improved safety and usability. Accordingly, information from the capacitance measuring unit may be shared with a control device of the release button 13 to unlock the button only upon correct removal of the release liner 31 or upon proper attachment to the skin as determined according to the disclosed implementations. Information from the capacitance measuring unit may also be conveyed to a user or patient via the status indicator 14. For instance, a first visual signal may be emitted for an approach to the body with the release liner attached ("finding an injection location"), a second signal for removing the release liner ("ready to attach"); a third signal for attachment to the body ("attached"); and a forth signal for removing the device from the body.

While the invention has been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

1 Device housing
10 Cover housing part
11 Window
12 Bottom housing part.
13 Release button
14 Optical indicator
2 Capacitive sensor
20, 21, 22 Aperture electrode
23 Auxiliary electrode
24 Sensor interface
30 Adhesive patch
31 Release liner
310 Release liner tab
311, 312 Conductive area
313 Non-conductive layer
32 Auxiliary foil or layer
34 Aperture
35 Cannula or injection needle
36 Capacitance measuring unit

What is claimed is:

1. A patch delivery device, comprising:
a bottom housing part;
a cannula or injection needle for subcutaneous delivery of a liquid to a patient;
an adhesive patch for adhering the bottom housing part to a patient's skin;
a capacitive sensor comprising a plurality of electrodes coupled to a capacitance measuring unit; and
a release liner covering a patient-side adhesive layer of the adhesive patch prior to adhering the bottom housing part to the patient's skin, wherein the release liner comprises at least one conductive area arranged on a surface of a non-conducting layer of the release liner.

2. The patch delivery device of claim 1, wherein the plurality of electrodes comprises at least one aperture electrode and an auxiliary electrode arranged adjacent to separate halves of a skin contact area of the bottom housing part, wherein the at least one conductive area of the release liner extends over at least a portion of the at least one aperture electrode and at least one portion of the auxiliary electrode.

3. The patch delivery device of claim 1, wherein the plurality of electrodes comprises a first aperture electrode and a second aperture electrode arranged on opposite sides of an aperture of the adhesive patch corresponding to a location of the cannula or injection needle, wherein the at least one conductive area of the release liner extends over at least a portion of the first aperture electrode and a portion of the second aperture electrode.

4. The patch delivery device of claim 1, wherein the plurality of electrodes comprises at least a first aperture electrode and a second aperture electrode, wherein the at least one conductive area of the release liner covers at least a portion of the first aperture electrode and at least a portion of the second aperture electrode, and wherein the release liner covers the first aperture electrode to a different extent compared to the second aperture electrode.

5. The patch delivery device of claim 1, wherein the device is configured as a patch injection device or as a wearable bolus injector.

6. The patch delivery device of claim 1, wherein at least the plurality of electrodes of the capacitive sensor form a part of the adhesive patch.

7. The patch delivery device of claim 1, wherein the capacitance measuring unit of the delivery device is configured to measure a signal indicative of a self-capacitance for each of the electrodes of the plurality of electrodes.

8. The patch delivery device of claim 1, wherein the at least one conductive area is printed, or coated, or glued, or otherwise applied onto the surface of a non-conducting layer of the release liner.

9. The patch delivery device of claim 1, wherein the plurality of electrodes comprises at least three aperture electrodes arranged in a circle around an aperture of the adhesive patch corresponding to a location of the cannula or injection needle.

10. A sensor patch for a patch delivery device, comprising:
a bottom housing part;
a cannula or injection needle for subcutaneous delivery of a liquid to a patient comprising an adhesive patch for adhering to the bottom housing part;
a capacitive sensor comprising a plurality of electrodes integrated in or printed onto the adhesive patch, and adapted to be connected to a capacitance measuring unit of the delivery device; and
a release liner comprising a non-conductive layer covering a patient-side layer of the adhesive patch, and at least one conductive area arranged on a surface of the non-conductive layer.

11. The sensor patch of claim 10, wherein the plurality of electrodes comprises an aperture electrode and an auxiliary electrode separated from each other at a distance of at least half a largest linear dimension of the sensor patch, wherein the at least one conductive area of the release liner extends over at least a portion of the aperture electrode and at least a portion of the auxiliary electrode.

12. The sensor patch of claim 10, wherein the plurality of electrodes comprises at least a first aperture electrode and a second aperture electrode arranged on opposite sides of an aperture of the adhesive patch corresponding to a location of the cannula or injection needle, wherein the at least one conductive area of the release liner extends over at least a portion of the first aperture electrode and at least a portion of the second aperture electrode.

13. The sensor patch of claim 10, wherein the plurality of electrodes comprises at least a first aperture electrode and a second aperture electrode, wherein the at least one conductive area of the release liner covers at least a portion of the first aperture electrode and at least a portion of the second aperture electrode, and wherein the release liner covers the first aperture electrode to a different extent compared to the second aperture electrode.

14. The sensor patch of claim 10, wherein the patient-side layer of the adhesive patch is an adhesive layer for adhering the sensor patch to the skin of the patient.

15. The sensor patch of claim 10, wherein the conductive area is printed, or coated, or glued, or otherwise applied onto the surface of a non-conductive layer of the release liner.

16. A patch delivery device, comprising:
a bottom housing part;
a cannula or injection needle for subcutaneous delivery of a liquid to a patient;
an adhesive patch for adhering the bottom housing part to a patient's skin comprising a capacitive sensor, the capacitive sensor comprising a plurality of electrodes adapted to be connected to a capacitance measuring unit of the delivery device; and
a release liner covering a patient-side adhesive layer of the adhesive patch prior to adhering the bottom housing part to the patient's skin, wherein the release liner comprises at least one conductive area arranged on a surface of the release liner and extending over at least a portion of the plurality of electrodes.

17. The patch delivery device of claim 16, wherein the plurality of electrodes comprises at least a first electrode and a second electrode separated from each other at a distance of at least half a largest linear dimension of the adhesive patch.

18. The patch delivery device of claim 17, wherein the plurality of electrodes further comprises a third electrode arranged adjacent to the first electrode, and wherein the release liner covers the first electrode to a different extent compared to the third electrode.

* * * * *